(12) United States Patent
Hilton et al.

(10) Patent No.: US 10,463,339 B2
(45) Date of Patent: Nov. 5, 2019

(54) ARTEFACT FOR EVALUATING THE PERFORMANCE OF AN X-RAY COMPUTED TOMOGRAPHY SYSTEM

(71) Applicant: Nikon Metrology NV, Heverlee (BE)

(72) Inventors: Daniel Hilton, Aylesbury (GB); Diego Alfredo Punin Albarracin, Berkhamsted (GB)

(73) Assignee: Nikon Metrology NV, Heverlee (BE)

( * ) Notice: Subject to any disclaimer, the term of this patent is extended or adjusted under 35 U.S.C. 154(b) by 0 days.

(21) Appl. No.: 14/759,500

(22) PCT Filed: Feb. 6, 2014

(86) PCT No.: PCT/EP2014/052344
§ 371 (c)(1),
(2) Date: Jul. 7, 2015

(87) PCT Pub. No.: WO2014/122218
PCT Pub. Date: Aug. 14, 2014

(65) Prior Publication Data
US 2015/0342559 A1    Dec. 3, 2015

Related U.S. Application Data (60) Provisional application No. 61/763,515, filed on Feb. 12, 2013.

(30) Foreign Application Priority Data

Feb. 11, 2013    (EP) .................................... 13154760

(51) Int. Cl.
*G01D 18/00*    (2006.01)
*A61B 6/08*    (2006.01)
(Continued)

(52) U.S. Cl.
CPC .............. *A61B 6/583* (2013.01); *A61B 6/032* (2013.01); *G01B 15/02* (2013.01); *G01N 23/046* (2013.01)

(58) Field of Classification Search
CPC ......... A61B 6/032; A61B 6/583; A61B 6/505; A61B 6/4423; A61B 6/508; A61B 6/482;
(Continued)

(56) References Cited

U.S. PATENT DOCUMENTS

| 4,892,197 A | 1/1990 | Slattery et al. |
| 5,745,545 A * | 4/1998 | Hughes .................... A61B 6/08 378/206 |

(Continued)

FOREIGN PATENT DOCUMENTS

| DE | 102005033187 A1 | 1/2007 |
| DE | 102006014509 A1 | 9/2007 |

(Continued)

OTHER PUBLICATIONS

PCT Notification Concerning Transmittal of International Preliminary Report on Patentability and Written Opinion of the International Searching Authority dated Aug. 20, 2015 in connection with PCT International Patent Application No. PCT/EP2014/052344, 7 pages.

(Continued)

*Primary Examiner* — Irakli Kiknadze
(74) *Attorney, Agent, or Firm* — Amster, Rothstein & Ebenstein LLP (57) ABSTRACT

The invention provides a kit for assembly of an artifact for evaluating performance purposes of an X-ray CT metrology system. The artifact comprises one or more interconnectable, stackable support plates, onto which a plurality of spherical bodies is mounted. The lightweight stacked support plate structure allows for a plurality of different con- (Continued)

figurations, and can be disassembled for enhanced storage, and safe and compact transportation.

18 Claims, 2 Drawing Sheets

(51) Int. Cl.
*A61B 6/00* (2006.01)
*G01B 15/02* (2006.01)
*G01N 23/046* (2018.01)
*A61B 6/03* (2006.01)

(58) Field of Classification Search
CPC ......... A61B 5/4509; A61B 6/563; A61B 6/14; A61B 6/502; A61B 6/542; A61B 6/585; A61B 5/002; A61B 5/0022; A61B 5/7264; A61B 6/4441; A61B 6/5205; A61B 8/08; A61B 2017/22034; A61B 2090/367; A61B 2090/3983; A61B 34/20; A61B 6/12; A61B 6/027; A61B 6/466; A61B 2017/00712; A61B 6/02; A61B 6/06; A61B 6/4007; A61B 6/40; A61B 8/587; A61B 6/03; A61B 8/0883; A61B 8/12; A61B 8/488; A61B 2017/00716; A61B 2017/00725; A61B 2034/2051; A61B 2034/2055; A61B 2090/376; A61B 90/39; A61B 2034/2072; A61B 2090/3937; A61B 90/36; A61B 5/055; A61B 6/037; A61B 2017/306; A61B 2090/363; A61B 5/0044; A61B 5/0813; A61B 5/416; A61B 6/00; G01B 15/02; G01B 21/042; G01B 3/30; G01N 2223/3035; G01N 23/046; G01N 23/083; G01N 23/04; A61L 27/18; A61L 2430/38; C08L 71/00
USPC ............................... 378/4, 62, 18, 207, 205
See application file for complete search history.

(56) References Cited

U.S. PATENT DOCUMENTS

| | | | | |
|---|---|---|---|---|
| 5,769,861 | A * | 6/1998 | Vilsmeier | A61B 6/12 600/426 |
| 6,493,574 | B1 * | 12/2002 | Ehnholm | A61B 5/055 378/18 |
| 6,527,443 | B1 * | 3/2003 | Vilsmeier | A61B 6/12 378/205 |
| 6,585,412 | B2 * | 7/2003 | Mitschke | A61B 6/547 378/207 |
| 6,626,569 | B2 * | 9/2003 | Reinstein | A61N 5/1048 250/252.1 |
| 7,613,501 | B2 * | 11/2009 | Scherch | A61B 5/064 378/65 |
| 7,907,699 | B2 * | 3/2011 | Long | A61N 5/1049 378/65 |
| 2003/0095637 | A1 * | 5/2003 | Sabczynski | A61B 6/583 378/207 |
| 2003/0095638 | A1 * | 5/2003 | Sabczynski | A61B 6/583 378/207 |
| 2003/0161442 | A1 * | 8/2003 | Zeiss | A61B 6/583 378/207 |
| 2013/0104678 | A1 * | 5/2013 | Ni | G09B 23/286 73/866.4 |

FOREIGN PATENT DOCUMENTS

| | | |
|---|---|---|
| DE | 102006028452 A1 | 12/2007 |
| JP | S58177514 A | 10/1983 |
| JP | 61-034207 A | 3/1986 |
| JP | 03-000045 A | 7/1991 |
| JP | 2003180666 A | 7/2003 |
| JP | 2011239830 A | 12/2011 |

OTHER PUBLICATIONS

International Search Report dated Apr. 9, 2014 for PCT Application No. PCT/EP2014/052344, 4 pages.

Kiekens K et al., "Parameter Dependent Thresholding for Dimensional X-ray Computed Tomography," Digital Industrial Radiology and Computed Tomography—Poster 12, 2011, 8 pages.

Lettenbauer H et al., "Means to Verify the Accuracy of CT Systems for Metrology Applications (In the Absence of Established International Standards," International Symposium on Digital Industrial Radiology and Computed Tomography, Jun. 25-27, 2007, 6 pages.

Yang K et al., "A geometric calibration method for cone beam CT sytems," Med Phys., 2006, Jun.; 33(6): 1695-1706.

Zhao J et al., "Geometric Parameters Estimation and Calibration in Cone-Beam Micro-CT," Sensors 2015, 15, 22811-22825.

Office Action dated Aug. 8, 2017 in connection with Japanese Patent Application No. 2015-556494, 6 pages.

* cited by examiner

ARTEFACT FOR EVALUATING THE PERFORMANCE OF AN X-RAY COMPUTED TOMOGRAPHY SYSTEM

CROSS-REFERENCE TO RELATED APPLICATIONS

This application is a U.S. national stage entry under 35 U.S.C. § 371 of PCT International Patent Application No. PCT/EP2014/052344, filed Feb. 6, 2014, which claims priority to European Patent Application No. 13154760.6, filed Feb. 11, 2013 and U.S. Provisional Patent Application No. 61/763,515, filed Feb. 12, 2013, the contents of all of which are herein incorporated by reference.

FIELD OF THE INVENTION

The present invention relates to an artefact that is a dimensional gauge to be used for evaluating performance of an X-ray metrology CT system.

BACKGROUND OF THE INVENTION

Like other metrology technologies, X-ray computed tomography (CT) systems must be traceably calibrated in order to deliver true metrological performance. Many of the errors affecting CT-systems need an adequate calibration of the machine reducing systematic errors. Although being in the pending process of developing calibration standards, there is currently no internationally recognized standardized procedure for calibrating X-ray CT metrology equipment. Instead, calibration must be derived and traced from another metrology method having such a standard, for example, an optical scanner or a touch probe attached to a coordinate measuring machine arm (CMM arm).

A preferred calibration method should be relatively low-cost and simple, and therefore relies on having a traceable calibration piece consisting of a number of spheres, which are chosen to have scale and X-ray properties similar to those of the test piece.

Typically the centre-to-centre distances of the spheres of calibration piece are measured by the X-ray CT instrument and compared with measurement data of the calibration piece obtained by another metrological method. Using spheres is absolutely required, since a linear threshold dimension would compromise accuracy.

Sphere gauges are well known from the art as calibration artefact, and are particularly recommended for presenting a minimum deviation of the measured length. Their spherical shape provides a self-centring line of contact. Results of experiments on the use of dedicated reference calibration artefacts are published, and according to the paper "Analysis of the error sources of a Computer Tomography Machine", by V. Andreu et al., a 27-sphere gauge shows to be very suitable to determine e.g. size measurement error because it is measured at different heights and the error appears to be independent on the position of the interest region on the detector.

Having measured the calibration piece, the exact scaling of the CT data can be performed so that it matches actual part dimensions and the voxel size of the 3D model being set to the value found from the traceable calibration. A traceable calibrated 3D CT-model is delivered after mapping with a true local surface determination.

Some designs in the prior art employ multiple styli with ruby spheres mounted onto a heavyweight block; this calibration artefact is rather large to store or to transport for executing calibration tests in the field. Because of the mounted styli, being thin, the calibration piece is also of a fragile construction, particularly difficult when packaging or transportation is required. Furthermore, assembly of this piece is prone to error, the large range of different heights adding an extra dimension to the calibration requirement, providing probe access problems.

DE 10 2005 033187 describes a two plate calibration artefact that stands vertically on a turntable. With the arrangement of balls, beam hardening is inevitable, and its thickness implies a limited useful in terms of calibrating several parameters. DE 10 2006 028 452 describes a calibration block machined from solid metal and provided with a plurality of surface calibration indentations. The necessary thickness also means a limited usefulness in terms of calibrating several parameters. DE 10 2006 014 509 describes a calibration block for a co-ordinate measurement machine.

The gauges for calibration and/or verification of the art have one fixed set-up that obliges use of the format with specifications as given, and does not allow for any adjustment or fine-tuning during the calibration procedure. Moreover, the geometry of X-ray CT instruments vary depending on the application, necessitating a plurality of different artefacts.

Therefore, there is a need for a more flexible artefact.

SOME EMBODIMENTS OF THE INVENTION

Figure 1:
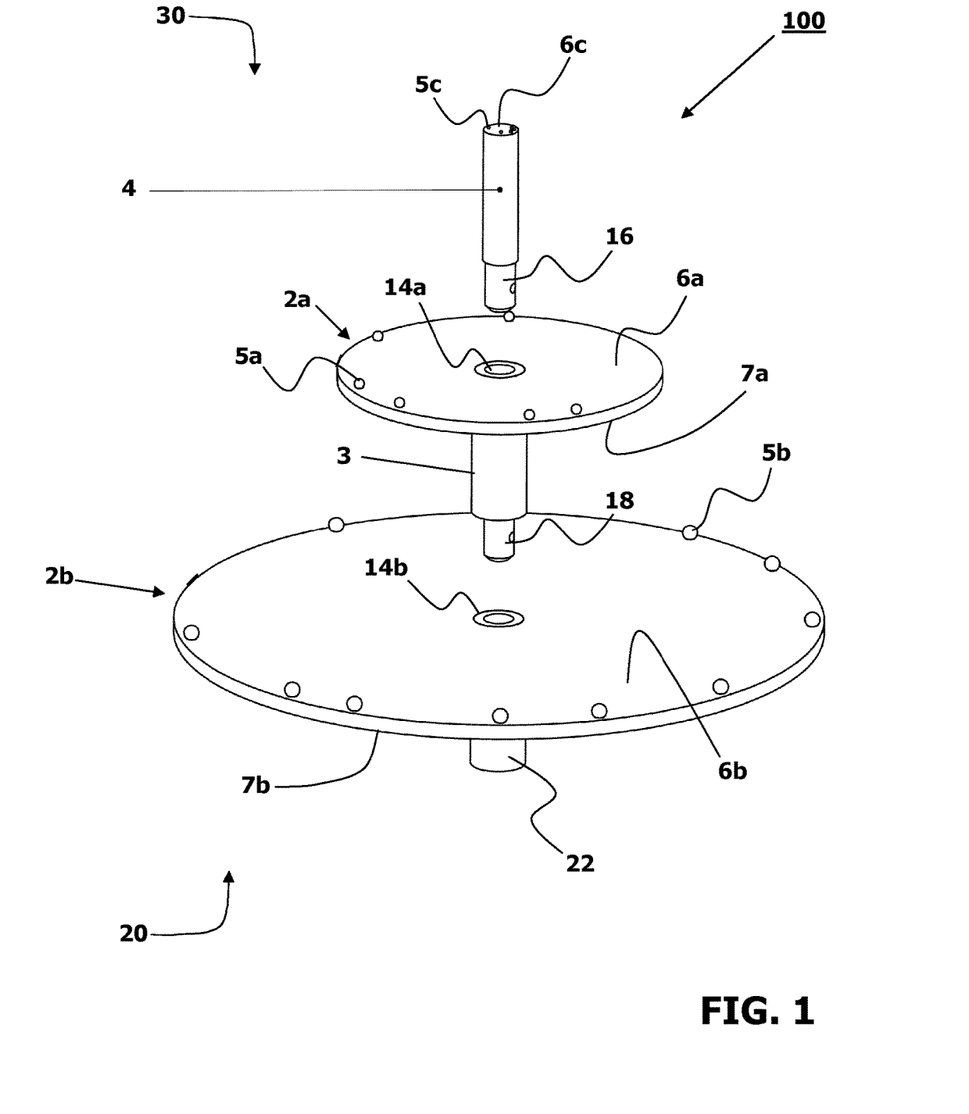
FIG. 1: Schematic representation of the stacked disc plates artefact

The invention provides a new type of artefact and kit for assembling it for evaluating performance purposes of an X-ray CT metrology system, as defined below. Reference is made to FIG. 1 by way of example.

On embodiment of the invention relates to a kit for assembly of different configurations of an artefact (100) for evaluating the performance of an X-ray computed tomography instrument, which kit comprises two or more interconnectable, stackable support plates (2a, 2b) each having a different area and provided with at least one spherical body (5a, 5b), wherein each spherical body (5a, 5b) is attached to the support plate (2a, 2b) on a surface (6a, 6b, 7a, 7b) of said support plate (2a, 2b).

The kit may further comprise a spacer (3) configured to align an adjacent pair of the support plates (2a, 2b) in the stack and for dismountable attachment to one or both of said adjacent pair of support plates (2a, 2b).

The spacer (3) may be non-dismountably attached at one end to one support plate (2a) and is dismountably attachable at the other end to another support plate (2b) to form the adjacent pair.

The kit may further comprise an end piece (4) configured for dismountable attachment to any one of the support plates (2a, 2b), which end piece (4) is provided with one or more further spherical bodies (5c), wherein each spherical body (5c) is attached to the end piece (4) on a surface (6c) of said end piece (4). The end piece (4) may terminate the stackability of the support plates (2a, 2b). The end piece (4) may be made at least partially from graphite. The end piece (4) may be a longitudinal member. The end piece (4) and spacer (3) may be aligned in the assembled calibration artefact (100) along a linear axis. The number of end pieces (4) may be one. The support plates (2a, 2b) may be circular. The support plates (2a, 2b) may be made at least partially from carbon fibre composite material. The kit may be configured such that the end piece (4) stands vertical in the assembled artefact. The kit may be configured such that none of the pair-wise distances between the centres of the spherical bodies is the same in the assembled artefact. The present invention further relates to a use of a kit according as described herein for calibration and/or verification of an X-ray computed tomography instrument. The present invention further relates to an artefact (100) assembled from a kit as defined herein.

Another embodiment of the invention relates to a calibration artefact (100) for calibrating an X-ray computed tomography instrument, comprising:
one or more support plates (2a, 2b), and
at least two spherical bodies (5a, 5b),
wherein each spherical body is attached to one of said support plates (2a, 2b) on a surface (6a, 6b, 7a, 7b) of said support plate (2a, 2b).

The calibration artefact (100) may comprise two or more stacked support plates (2a, 2b), wherein each adjacent pair of support plates (2a, 2b) in the stack is separated by a spacer (3), wherein the spacer (3) separating each adjacent pair of support plates (2a, 2b) is configured for dismountable attachment to one or both of said adjacent support plates (2a, 2b).

The calibration artefact (100) may comprise may have a base end (20) and an upper end (30), and further comprise an end piece (4) at the upper end (30) of the artefact (100) which end piece (4) is provided with one or more further spherical bodies (5c).

The end piece (4) may be configured for dismountable attachment to the support plate (2a) at the upper end (30) of the artefact (100).

The calibration artefact (100) may comprise may have a base end (20) and an upper end (30), and further comprise a stand (22) rigidly attached to the support plate (2b) at the base end (20) of the artefact (100). The end piece (4), spacer(s) and stand may be aligned in the calibration artefact along a linear axis. The support plates may be planar, and circular or oval. The artefact may be disposed with least three spherical bodies, and the pair-wise distances between at least three of these spherical bodies are not the same. The spherical bodies may be corundum spheres, preferably ruby spheres, or a mixture of these. Each spherical body may be attached to one of said support plates (2a, 2b) on a surface (6a, 6b, 7a, 7b) of said support plate (2a, 2b) using an adhesive bond. The stacked support plates (2a, 2b) may each have an upper (6a, 6b) and lower surface (7a, 7b), and the upper surface may be utilised for attachment of a spherical body. The stacked support plates (2a, 2b) may each have an upper (6a, 6b) and lower surface (7a, 7b), and the spherical bodies may be arranged around the periphery of the upper surface. The supporting plates (2a, 2b) and said spacer (3) may be made at least partially from carbon fibre composite material. At least two of supporting plates (2a, 2b) adjacently arranged may be mutually parallel. At least one of the supporting plates may be tilted, optionally oriented at an angle of +70 to +110 deg with respect to a central axis of an adjoining spacer (3). None of the pair-wise distances between the centres of the spherical bodies may be the same.

DETAILED DESCRIPTION OF THE INVENTION

Before the present system and method of the invention are described, it is to be understood that this invention is not limited to particular systems and methods or combinations described, since such systems and methods and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the present description of the invention, reference is made to the accompanying drawings that form a part hereof, and in which are shown by way of illustration only of specific embodiments in which the invention may be practiced. Parenthesized or emboldened reference numerals affixed to respective elements merely exemplify the elements by way of example, with which it is not intended to limit the respective elements. It is to be understood that other embodiments may be utilised and structural or logical changes may be made without departing from the scope of the present invention. The following detailed description, therefore, is not to be taken in a limiting sense, and the scope of the present invention is defined by the appended claims.

Due to multiple materials used in the prior art, and a densely packed construction, there are many obstacles along the propagation path of the X-ray beam, composed of individual photons with a range of energies. As the beam passes through an object, it becomes harder, meaning that the energy increases, because the lower-energy photons are absorbed more rapidly, leaving behind only the high-energy photons. The effect of beam hardening concerns the non-linear attenuation of the X-ray beam along propagation through an object due to the polychromatic character of the spectrum and the energy dependent X-ray attenuation. As a result, so-called cupping artefacts, or streaks or dark bands between dense objects will degrade the image quality. Therefore, there is a need for a simple, and minimally used materials and components design artefact.

The present invention relates to a kit for assembling artefact (100) for measuring and evaluating the performance of an X-ray computed tomography (CT) system, especially for metrology. The present invention also relates to the artefact (100) for measuring and evaluating the performance of an X-ray computed tomography (CT) system, especially for metrology.

With reference to FIG. 1, the artefact and/or kit comprises at least one, preferably at least two stacked support plates (2), wherein one or more spherical bodies (5a, 5b) are mounted on each plate. The artefact has a base end (20) and an upper end (30). The support plate may comprise an upper surface and a lower surface, and is provided with a plurality of spherical bodies, for example on the periphery of the upper surface. Each adjacent pair of support plates (2a, 2b) is separated by a spacer (3). It is preferred that one or both support plates (2a, 2b) flanking a spacer (3) is dismountable from the spacer (3). The assembled artefact (100) preferably stands essentially vertically, the base-end (20) at the bottom and the upper-end (30) at the top.

The positions, more specifically the distances of at least some, preferably all of the spherical bodies present in the artefact are measured using a measurement device such as an optical scanner or touch probe attached to a co-ordinate measuring machine arm. The artefact can be used for evaluating the performance of an X-ray metrology CT system, namely, for calibration, and/or verification and/or identification and correction of errors within the X-ray metrology CT system. Knowledge of the distances between the spheres can be used for the verification and calibration of an X-ray metrology CT system, by comparing the measurement obtained from the CT system with the measurement obtained with the measurement device. The artefact increases accuracy, and allows calibration, for instance, in accordance with the VDI 2630 guidelines, concerning fundamentals, terms and procedures that are needed when using computed tomography for dimensional measurements in industrial environments. The dismountable construction enables ease of storage and transport, and makes available a plurality of different configurations. The direct mounting of the rubies onto the plates, avoiding intermediate structures, allows less possibility for structural distortions so reducing the need to frequently measure the artefact.

The support plates (2, 2a, 2b) each have an upper and lower surface. A support plate acts as a supporting substrate for the spherical bodies. The upper surface points in the direction of the upper-end (30) and the lower surface points in the direction of the base end (20). There may be at least 1 plate, preferably 2, 3, 4, 5, 6, 7, 8, 9, 10 or more stacked support plates in the kit and/or artefact, preferably 2 plates (2a, 2b). Each adjacent pair of support plates in the stack is preferably mutually parallel. A support plate is preferably circular in shape, though other shapes are envisaged, such as oval. A support plate is preferably rigid. A support plate may be planar or non-planar.

Preferably, the size of at least two, preferably all of the support plates are not the same. It is preferred that the artefact has a base end (20) and an upper end (30), and the size of the stacked support plates diminishes from the base end to the upper end. Where the support plates are circular, preferable the diameter of the stacked support plates diminishes from the base end to the upper end. It will be appreciated that the areas of the support plates are correspondingly different, for instance, the sum of the upper and lower surfaces of each plate are different.

At least two of the supporting plates adjacently arranged may be mutually parallel. At least one of the supporting plates may be tilted. At least one, optionally all of the supporting plates may be oriented at an angle of +50 to +120 deg, preferably +70 to +110 deg with respect to a central axis of an adjoining spacer (3).

The support plates (2a, 2b) are interconnectable, meaning that a support plate is capable of dismountable attachment to one (2b) or two (2a) adjacent plates. At least one, preferably each and every support plate (2a, 2b) may be disposed with a plate coupling (14a, 14b) configured to receive and dismountably attach to a reciprocating coupling on adjacent plate or on an end piece (4). Specifically, at least one, preferably each and every support plate (2a, 2b) may be disposed with a plate coupling (14a, 14b) configured to receive and dismountably attach to a reciprocating coupling (18) of a spacer (3) or a coupling (16) of an end piece (4). The plate coupling (14a, 14b) is preferably identical for each support plate (2a, 2b). Each support plate may be disposed with 1, 2 or more couplings, preferably with one. The plate coupling (14a, 14b) may be incorporated into a spacer (18) or stand (22) that is rigidly attached to the plate (2a).

Preferably the plate coupling (14a, 14b) is disposed at a point that is the centre of gravity of the support plate. When the support plate is circular, preferably the plate coupling (14a, 14b) is provided at the centre of the circle.

Preferably the distance between adjacent pairs of support plates (2a, 2b) is the same in the artefact (100). Preferably the distances between adjacent pairs of support plates (2a, 2b), in addition to the distance between uppermost support plate and the upper terminal end (6c) of the end piece (4) are the same.

The support plate layout allows the selection of the preferred substrate material in relation to ideal thermal properties. As an example, the support plate (2a, 2b) may be constructed at least partially, preferably entirely from a dense material such as Invar. The support plate (2a, 2b) may be constructed at least partially, preferably entirely from an X-ray transparent material such as carbon fibre composite. Carbon fibre composite, as known from the art, is a material widely used in CT scanning applications due to its high penetrability rate to X-rays. In addition, carbon fiber has a very low coefficient of thermal expansion, which makes measurements repeatable at variable temperatures and atmospheric conditions.

When using a thin support plate, the X-ray beam propagates in a more open design with less material present. Hence, the X-ray beam has less opportunity to collide with material, thereby reducing the occurrence of beam hardening.

The present invention not only provides less material using the stacked plates configuration, but also comprises less different materials compared to the art, e.g. by eliminating styli on which spherical bodies are mounted, and thereby further decreasing the effect of beam hardening, where a mixture of materials in the X-ray CT system causes interference and reduction of accuracy due to the polychromatic nature of the X-ray sources used.

The support plate (2a) at the upper end (30) of the artefact (100) may be provided with an end piece (4). The end piece (4) may function as a handle allowing the artefact (100) to be gripped by a human or robot hand or fingers. Such handle may prevent forces being applied to the outer edges of the support plates (2a, 2b) during transport which would lead to structural distortions. The end piece (4) may, alternatively or additionally, function as a measurement pillar, providing a supporting substrate for the attachment of further spherical bodies, as set out below.

The end piece (4) may provide a supporting substrate for the attachment of further spherical bodies in addition to those on the supporting plates (2a, 2b). In particular the upper terminal end (6c) of the end piece (4) may provide a surface for this purpose. The upper terminal end (6c) of the end piece (4) is the surface of the end piece (4) at the upper terminal end; it typically has a circular profile. The upper terminal end of the end piece (4) may be planar or non-planar. The upper terminal end of the end piece (4) is preferably planar. The planar upper terminal end of the end piece (4) may be perpendicular to a central axis of the end piece.

The end piece (4) is preferably a rigid member. Preferably the end piece (4) is an elongated member. The end piece (4) is preferably a cylindrical elongated member. The end piece (4) is preferably linear. The end piece (4) may be solid or hollow.

It is preferable that the end piece (4) is dismountably attached or attachable to a support plate (2a, 2b), preferably to the upper end support plate (2a). A dismountable attachment allows for the ease of dismantling, storage and transport of the artefact, and of assembling alternative configurations. One end of the end piece (4) may be provided with a dismountable end piece (4) coupling (16) for attaching to a reciprocating plate coupling (14a, 14b) on the support plate. This coupling end of the end piece (4) provided with a dismountable end piece coupling (16) is opposite the upper terminal end (6c) of the end piece (4). As previously mentioned, the plate coupling (14a, 14b) may be incorporated into a spacer (18) or stand (22) that is rigidly attached to the plate (2a, 2b). The end piece (4) preferably terminates the stackability of the support plates. The upper terminal end (6c) of the end piece (4) is preferably not disposed with a coupling receive and dismountably attach to a coupling (18) of a spacer (3) or a coupling (16) of a further end piece (4).

The end piece (4) may be made from the same material as the support plates, or made from a different material. Preferably the end piece (4) is made at least partially, preferably entirely from graphite or from a carbon fibre composite material.

The spherical body used in the invention may be made from any material suitable for calibration or verification, depending on the power or section of the X-ray spectrum used. Preferred materials for the spherical body may be selected from the group comprising: corundum (such as ruby and sapphire), tungsten carbide, stainless steel, and ceramics. A spherical body may be hollow or solid, preferably solid. A spherical body is CT-detectable.

In a preferred embodiment, the spherical body is a corundum sphere, preferably a ruby sphere. A ruby sphere has the advantage of being relatively inexpensive and of being obtainable at very high tolerances. The spherical body may be of any particular grade, colour, hardness, or treatment. In an embodiment, the spherical body comprise or consist of synthetic corundum.

The artefact (100) may contain at least two spherical bodies, preferably at least three spherical bodies (5a, 5b, 5c), each preferably being a ruby sphere, for instance, 3, 4, 5, 6, 7, 8, 9, 10, 11, 12, 13 14, 15, 16, 17, 18, 19, 20, 21, 22, 23, 25, 26, 30, 35, 40, 45, 50, or more spherical bodies, or a number between any two of the aforementioned values, preferably 20 to 25 spherical bodies. Preferably, the artefact (100) comprises as many spherical bodies as possible without having a situation where the beam intersects more than two spherical bodies. The spherical bodies are distributed between support plates (2a, 2b), and end piece (4) where present.

Each support plate (2a, 2b) may be disposed with 1, preferably 2 or more (e.g. 3, 4, 5, 6, 7, 8, 9, 10), spherical bodies (5a, 5b), that are preferably ruby spheres. Preferably, the support plate disposed at the upper end (30) contains less spherical bodies compared with the support plate disposed at the lower end (20) of the artefact (100). The support plates may contain 15, 16, 17, 18, 19, 20, 21, 22, 23, 25, 26, 30, 35, 40 or more spherical bodies, or a number between any two of the aforementioned values, distributed amongst said support plates.

In an embodiment where spherical bodies are attached to a support plate, the spherical bodies are dispersed across one surface, preferable the upper of the support plate. In a preferred embodiment, at least one, preferably all such spherical bodies are attached at or towards the periphery of the upper or lower surface of said support plate. At least one, preferably all such spherical bodies are preferably arranged along a fictive circle disposed on the periphery of the upper and/or lower surfaces. At least one, preferably all such spherical bodies are preferably arranged along a fictive circle disposed on the periphery of the upper surface of the support plate.

Where the end piece (4) is present, a spherical body may be provided on the end piece (4). The end piece (4) where present may be disposed with 1, preferably 2 or more (e.g. 3, 4, 5, 6, 7, 8, 9, 10), most preferably 6 spherical bodies, that are preferably ruby spheres.

In an embodiment where spherical bodies are attached to the end piece (4), at least one, preferably all such spherical bodies are attached at or towards the periphery of the surface of the upper terminal end of said end piece (4). At least one, preferably all such spherical bodies are preferably arranged along a fictive circle disposed on the periphery of the surface of the upper terminal end of said end piece (4). In a preferred embodiment, the spherical bodies are dispersed across the entire surface of the upper terminal end of the end piece (4).

An artefact having at least one support plate, preferably two stacked support plates, and a end piece (4) may contain at least 3 spherical bodies, more preferably 6, 7, 8, 9, 10, 11, 12, 13, 14, 15, 16, 17, 18, 19, 20, 21, 22 or more spherical bodies (5a, 5b, 5c), that are preferably ruby spheres, distributed amongst the support plates and the end piece (4). Preferably, the artefact having two stacked support plates and a end piece (4) contains at least 22 spherical bodies (5a, 5b, 5c), 6 distributed on the end piece (4), 6 distributed on one support plate (2a) and 10 distributed on another support plate (2b). Preferably, the artefact having two stacked support plates and an end piece (4) contains at least 22 spherical bodies (5a, 5b, 5c), 6 distributed on the end piece (4) at the upper terminal end (6c), 6 distributed on the support plate (2a) at the upper end (30) of the artefact (100) and 10 distributed on another support plate (2b) at the base end (20) of the artefact (100).

Preferably the distance between any two spherical bodies in the artefact (100) is not identical. Preferably, the pair-wise distances of at least three of the spherical bodies are not identical. Preferably, the pair-wise distances of all the spherical bodies are not identical. The distance is preferably the centre-to-centre distance.

A spherical body is typically spherical. The outer diameter of a spherical body, that is preferably a ruby sphere, may typically be equal to or less than 0.5 mm, 0.7 mm, 1.0 mm, 1.2 mm, 1.4 mm, 1.6 mm, 1.8 mm, 2.0 mm, 2.2 mm, 2.4 mm, 2.6 mm, 2.8 mm, 3.0 mm, 3.2 mm, 3.4 mm, 3.6 mm, 3.8 mm, 4.0 mm, 4.2 mm, 4.4 mm, 4.6 mm, 4.8 mm, 5.0 mm, 5.2 mm, 5.4 mm, 5.6 mm, 5.8 mm, 6.0 mm, 6.2 mm, 6.4 mm, 6.8 mm, 7.0 mm, 7.2 mm, 7.4 mm, 7.6 mm, 7.8 mm, 8.0 mm, 8.2 mm, 8.4 mm, 8.6 mm, 8.8 mm, 9.0 mm, 9.2 mm, 9.4 mm, 9.6 mm, 9.8 mm, or 10.0 mm, or a value in the range between any two of the aforementioned values, preferably between 0.7 mm and 6.0 mm. The outer diameter may be measured using known methods.

Most preferably, a spherical body (5a, 5b, 5c) is directly attached to a support plate (2a, 2b) or end piece (4). In other words, a spherical body may be directly attached to a surface of support plate or end piece (4). Preferably, there is no additional member between the end piece (4) and the spherical body (5c). The spherical body (5c) may be attached to the flat surface of the support plate (2a, 2b) or end piece (4) e.g. it is not disposed in an indentation thereon. Alternatively, the spherical body (5c) may be attached to the flat surface of the support plate (2a, 2b) or end piece (4) in a shallow indentation. Such shallow indentation may have a depth of equal to or less than 50% of the diameter of the spherical body, preferably equal to or less than 20%, preferably between 10-20%.

The surface of the support plate (2a, 2b) or end piece (4) is preferably attached to the outer surface of the ruby using an adhesive. Preferably a spherical body (5a, 5b) is directly attached to an upper surface of a support plate. Preferably, there is no additional member between the support plate and the spherical body. Preferably, a spherical body (5c) is attached to the upper terminal end (6c) of the end piece (4). A spherical body is preferably attached to a support plate or end piece (4) by bonding. Preferably the attachment is fixed, and non-dismountable. A spherical body may be glued or attached directly to the surface of the plate or to the surface of the end piece (4) by any adhesive known in the art of being capable of bonding, such as an epoxy resin, preferably a two-component epoxy resin. This ensures long-term stability of the position of the spherical bodies.

Adjacent support plates (2a, 2b) in the stack may be separated by spacer (3). The spacer (3) is a rigid member attached either side to a different support plate (2a, 2b). Preferably a spacer is an elongated member. The spacer is preferably linear. A spacer is preferably a cylindrical elongated member. It may be solid or hollow. One spacer may be used to separate the support plates of an artefact comprising two stacked plates. Two spacers may be used to separate the plates of an artefact comprising three stacked plates. A spacer is provided between each pair of adjacent support plates, providing a tandem linear array of spacer and support plate, which terminates at both ends in a support plate. Optionally, the upper end (30) is disposed with a end piece (4), and the base end (30) is disposed with a stand (22). The spacer may be made from the same material as the support plates, or made from a different material. Preferably the spacer is made from at least partially, preferably entirely from a carbon fibre composite material.

Besides separating the support plates, the spacer may be configured to maintain the plates in fixed relation.

A spacer (3) may be dismountably attached or attachable to one or both adjacent support plates (2a, 2b). This allows for the ease of reconfiguring, dismantling, storage and transport of the artefact (100). It is envisaged that the artefact may be assembled and dissembled as required, and stored and transported in a suitcase. One or both ends of the spacer (3) may be provided with a dismountable spacer coupling (18) for attaching to a reciprocating plate coupling (14b) on the support plate. The spacer coupling may comprise a screw thread, a push fitting, male or female connector and the like. The spacer coupling (18) is preferably configured to position and lock adjacent plates in a fixed positional and rotational alignment.

It is preferable that the spacer (3) is rigidly or non-dismountably attached at one end to a support plate (2a) at the point its centre of gravity, and at the other end is provided with a dismountable coupling (18) for attaching to a reciprocating coupling (14b) on another support plate.

The support plate (2b) at the base end (20) of the artefact (100) may be provided with a stand (22) on which the artefact is supported from below. The stand (22) may allow the artefact (100) to be positioned on a fitting (e.g. rotating coupling) within the X-ray CT apparatus. The stand prevents forces being applied to the support plates (2b) at the base end (20) which would lead to structural distortions. The stand is preferably a rigid member. The stand may be an elongated member. The stand (22) may be cylindrical. The stand may be solid or hollow. The stand is preferably has a linear axis. The transverse cross-section area of the stand, i.e. perpendicular to its central axis, is preferably greater than the transverse cross-section area of a spacer. The stand may be dismountably attached to the base end (30) support plate (2b). It is preferable that the stand is rigidly or non-dismountably attached to the base end support plate (2b). It is preferable that the stand attached to the base end support plate (2b) at the point its centre of gravity. The stand may be made from the same material as the support plates, or made from a different material. Preferably the stand is made at least partially, preferably entirely from a carbon fibre composite material.

It is an aspect of the invention that the spacer(s) (3) and end piece (4) where present and stand (22) where present align in the assembled artefact along a longitudinal axis to form a continuous axis in the artefact (100) that is preferably linear. The spacer(s) (3) and end piece (4) where present and stand (22) where present are preferably mutually dismountably attached in a linear array. The end piece (4) may be configured for dismountable attachment to the spacer (3). The spacer (4) may be configured for dismountable attachment to the end piece (4) and to the stand (22). The stand (22) may be configured for dismountable attachment to the spacer (3).

It is preferred that the spacer (3) is rigidly attached at one end to a support plate (2a) and is provided with a coupling at the other end for dismountable attachment to another support plate (2b). The spacer (3) may be rigidly attached at one end to the support plate (2a) through a hole in the support plate (2a). A plate coupling (14a) may be provided in the spacer that is accessed through said hole.

It is preferred that the stand (22) is rigidly attached at one end to a support plate (2b). The stand (22) may rigidly attached at one end to the support plate (2b) through a hole in the support plate (2b). A plate coupling (14b) may be provided in the stand (22) that is accessed through said hole.

Thus, the central axes of the spacer(s) (3) and end piece (4) where present and stand (22) where present are aligned and form one central axis of the stacked plates assembled, whereby the spacer (3) act as a support between the stacked plates.

Figure 2:
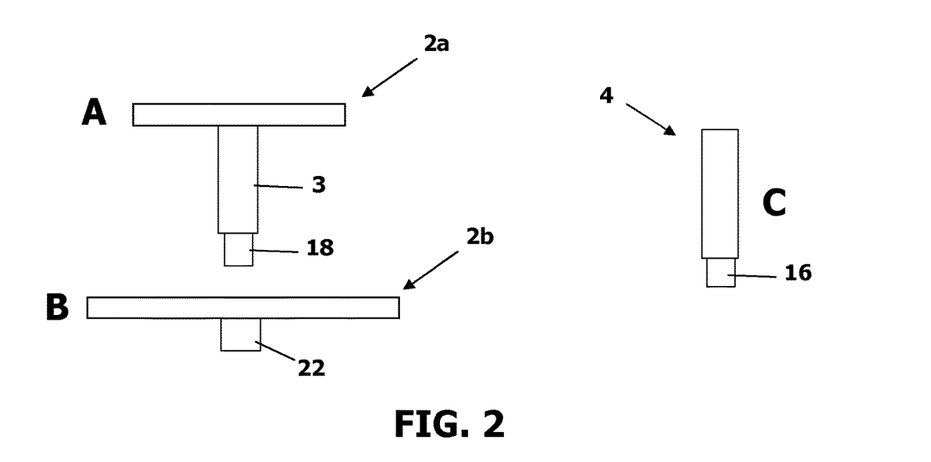
FIGS. 2A to C: Side view representations of kit components, namely an upper plate (A), a lower plate (B), and an end piece (C).
Figures 3, 4:
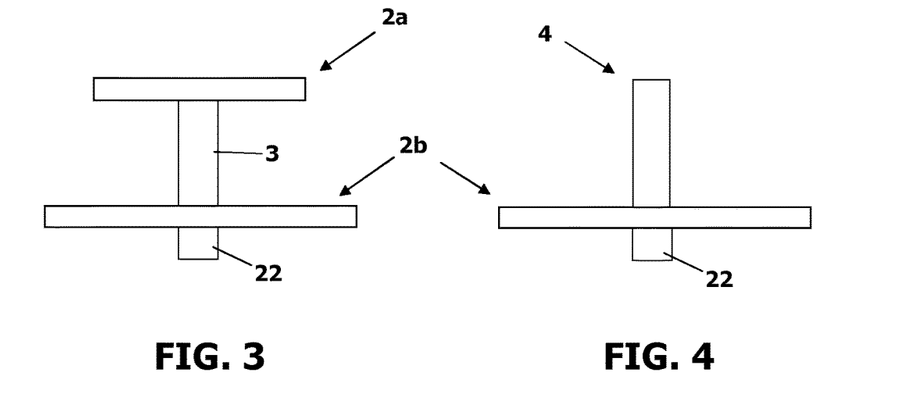
FIG. 3: one possible configuration of an artefact comprising one upper and one lower plate
FIG. 4: one possible configuration of an artefact comprising one lower plate and an end-piece.

With reference to FIGS. 2A to C, the kit of the invention comprises at least one, preferably at least two (e.g. 2, 3, 4, 5 or more) of the aforementioned support plates (2a, 2b), wherein one or more spherical bodies (not shown) are mounted on each plate. The support plates preferably have different sizes. One of the support plates (FIG. 2A, 2a) may be disposed with one of the aforementioned spacers (3), configured for dismountable attachment to an adjacent support plate (2b). The kit may further comprise an end piece (FIGS. 2C, 4) as described herein, configured for dismountable attachment to the uppermost support plate (2a or 2b) at the upper end (30) of the artefact (100). One, preferably all of the support plates (2a, 2b) may be disposed with the coupling (not shown) configured for dismountable attachment to a spacer (3) or end piece (4). A kit allows the user to select different configurations of the artefact. As shown in FIG. 3, two support plates of FIGS. 2A and 2B are interconnected. As shown in FIG. 4, the plates of FIG. 2B and the end piece of FIG. 2C are interconnected. The variation in sizes allows the calibration or setting of different parameters within the X-ray CT metrology system without the need to change the artefact within the measurement volume.

In an X-ray CT metrology system application, the artefact may be placed in the measurement space and scanned at varying geometric magnification positions. Through calculation of the measurement errors achieved with the artefact, the system can be calibrated, and/or verified and/or tested. In embodiments of the present invention, the stacked interchangeable plates structure allows for a large range of length measurements covering a full range of possible sample sizes using one single artefact, and thereby reducing cost and operator time needed to calibrate the system. Furthermore, in embodiments of the present invention, the stacked support plates layout allows, due to a large range of calibrated length measurements, an averaging out of measurement errors to better determine the accuracy of the system in terms of both length and probing errors.

X-ray CT metrology systems are measurement machines that rely on precise knowledge of the positioning of the sample in relation to the source and detector. This relationship determines the magnification of the shadow cast by the object on the X-ray detector. An object close to the source casts a larger shadow than the same object at the detector. This relationship is a 1/x relationship, so at large FOD (focal spot to object distance, i.e. source to object distance), a change in sample position would have little influence, but as the FOD becomes smaller (High magnification), the same change would significantly affect the measurement. As such, at higher magnifications, source to object distance (FOD) is highly critical to the CT systems measurement performance. At lower magnifications, the FOD is less critical. However larger measurement lengths at the object make the relationship of the FID (spot to image distance, i.e. source to detector distance) more critical. The artefact can be tailored according to the measurement volume of X-ray CT metrology system, and according to the parameter to be measured; it permits FOD measurement using the smaller support plate at very high magnification and FID measurement using the larger support plate at low magnification. It is generally considered in the field of metrology that the focal spot is the nominal average position from which the x-rays are considered to emit from, the image is the nominal average position of the centre point of the detector plane, and the object is the position of the centre of rotation of the object on the direct path between the focal spot and the detector centre point.

Additionally, with the large number of measurements possible from a single scan in embodiments of the present invention, the single artefact is not only used for calibration or verification, but is potentially also used to test the system based on the selection of alternating lengths within the sample plates of the artefact.

Additionally, the attachment of the spherical body directly to the surface of the support plate or end-piece allows measurement in several directions for a single material, thereby avoiding beam hardening that can lead to so-called cupping artefacts, or streaks or dark bands between dense objects will degrade the image quality.

The precise design used in embodiments of the present invention, overcomes following issues compared to the art. The support plates are easy to manufacture and can be made from a lightweight material, including those suitable for CT applications. The stacked disc configuration allows for ease of calibration or verification, both in terms of ease of setup and accuracy since a large portion of each spherical body is accessible for surface measurement. Furthermore, there is a reduced likelihood of glue contamination of the spherical bodies. Embodiments of present invention, with demountable nature of the construction, provide enhanced storage and transportation of the artefact while not affecting the measurement values.

The skilled person will understand how to configure the artefact according to the parameters that require testing. In other words, the size of the support plates, the number of support plates, the distance between the support plates and end piece if present, and the arrangement of spherical bodies can be determined with a knowledge of the X-ray CT instrument and the parameters to be tested. For instance, for a verification, the artefact may contain a support plate having an arrangement of spherical bodies providing a distance measurement of <30 mm, and up to 66% of the maximum measurement length of the X-ray CT. For a calibration, 1 or 2 or more additional support plates and optionally an end piece providing spherical bodies at the upper and lower extremes of measurement length for the system allow a determination of source and detector positions. The spatial separation between the respective support plates allow an identification of errors in alternative regions of the system, such as source position errors, and manipulator positioning and detector distortion errors.

A particular embodiment of the invention relates to an artefact having an upper end (30) and a base end (20) comprising:

two stacked support plates (2),
a spacer (3) separating the support plates, rigidly attached to the upper-end support plate,
a stand (22) rigidly attached to the base-end support plate, and
an end piece (4) at the upper-end,
a plurality of spherical rubies (5a, 5b, 5c) mounted on an upper surface (6a, 6b) of both support plates and on an upper terminal end (6c) of the end piece (4), and
wherein the end piece (4) is configured for dismountable attachment to the spacer, and the spacer is configured for dismountable attachment at one end to said end piece (4) and at another end to the stand.

The two stacked support plates (2) may be of different sizes. The spacer (3) may be attached to the plate (2b) at the base end (20) using a male/female dismountable coupling.

An end piece (4) is provided that is dismountable attached to the upper support plate, whereby the central axis of the end piece (4) coincides with the centre of the upper-most plate. The end piece (4) connection is part of the artefact assembly, and is also dismountable for enhanced storage and transportation. The central axis of the end piece (4) is aligned with the central axes of the spacer, and together can be seen as one virtual central axis of the artefact (12) configuration. The number of spherical rubies is preferably 22.

A particular embodiment of the invention relates to a kit for assembling an artefact having an upper end (30) and a base end (20) comprising:
two support plates (2) of different sizes,
a spacer (3) configured to separating the support plates (2),
a stand (22) configured to be disposed at the base-end, and
an end piece (4) configured to be disposed at the upper-end,
a plurality of spherical rubies (5a, 5b, 5c) mounted on an upper surface (6a, 6b) of both support plates and on an upper terminal end (6c) of the end piece (4), and
wherein the end piece (4) is configured for dismountable attachment to the spacer (3) or to the stand (22), and the spacer (3) is configured for dismountable attachment at one end to said end piece (4) and at another end to the stand (22).

The spacer (3) may be rigidly attached at one end to one support plate (2a), and at the other end dismountably attached to another support plate (2b) using a male/female dismountable coupling.

The present invention further relates to use of a kit or artefact (100) as described herein for evaluating the performance of an X-ray metrology CT system.

The present invention further relates to use of a kit or artefact (100) as described herein for calibration and/or verification of an X-ray metrology CT system.

The invention claimed is:

1. A kit for assembly of different configurations of an artefact (100) for evaluating the performance of an X-ray computed tomography instrument, which kit comprises two or more interconnectable, stackable support plates (2a, 2b) each having a different area and provided with at least one spherical body (5a, 5b), wherein each spherical body (5a, 5b) is attached to the support plate (2a, 2b) on an upper or lower surface (6a, 6b, 7a, 7b) of said support plate (2a, 2b) and is non-compliant.

2. The kit according to claim 1, further comprising a spacer (3) configured to align an adjacent pair of the support plates (2a, 2b) in the stack and for dismountable attachment to one or both of said adjacent pair of support plates (2a, 2b).

3. The kit according to claim 2, wherein the spacer (3) is non-dismountably attached at one end to one support plate (2a) and is dismountably attachable at the other end to another support plate (2b) to form the adjacent pair.

4. The kit according to claim 1, further comprising an end piece (4) configured for dismountable attachment to any one of the support plates (2a, 2b), which end piece (4) is provided with one or more further spherical bodies (5c), wherein each spherical body (5c) is attached to the end piece (4) on a surface (6c) of said end piece (4).

5. The kit according to claim 4, wherein the end piece (4) terminates the stackability of the support plates (2a, 2b).

6. The kit according to claim 4, wherein said end piece (4) is made at least partially from graphite.

7. The kit according to claim 4, wherein the end piece (4) is a longitudinal member.

8. The kit according to claim 4, wherein the number of end pieces (4) is one.

9. The kit according to claim 4 configured such that the end piece (4) stands vertical in the assembled artefact.

10. The kit according to claim 1, further comprising
a spacer (3) configured to align an adjacent pair of the support plates (2a, 2b) in the stack and for dismountable attachment to one or both of said adjacent pair of support plates (2a, 2b), and
an end piece (4) configured for dismountable attachment to any one of the support plates (2a, 2b), which end piece (4) is provided with one or more further spherical bodies (5c), wherein each spherical body (5c) is attached to the end piece (4) on a surface (6c) of said end piece (4),
wherein the end piece (4) and the spacer (3) are aligned in the assembled artefact (100) along a linear axis.

11. The kit according to claim 1, wherein the support plates (2a, 2b) are circular.

12. The kit according to claim 1, wherein said support plates (2a, 2b) are made at least partially from carbon fibre composite material.

13. The kit according to claim 1 configured such that none of the pair-wise distances between the centres of the spherical bodies is the same in the assembled artefact.

14. Use of a kit according to claim 1 for calibration and/or verification of an X-ray computed tomography instrument.

15. An artefact (100) assembled from a kit as defined in claim 1.

16. The kit according to claim 1, wherein each non-compliant spherical body is a corundum, tungsten carbide, stainless steel or ceramic spherical body.

17. The kit according to claim 16, wherein the corundum spherical body is a ruby or sapphire spherical body.

18. The kit according to claim 16, wherein the corundum spherical body comprises synthetic corundum.

* * * * *